United States Patent [19]

Vielkind

[11] Patent Number: 5,719,032
[45] Date of Patent: Feb. 17, 1998

[54] MELANOMA AND PROSTATE CANCER SPECIFIC ANTIBODIES FOR IMMUNODETECTION AND IMMUNOTHERAPY

[75] Inventor: Juergen R. Vielkind, British Columbia, Canada

[73] Assignee: University of British Columbia, Vancouver, Canada

[21] Appl. No.: 654,641

[22] Filed: May 28, 1996

Related U.S. Application Data

[63] Continuation-in-part of Ser. No. 829,855, Jan. 31, 1992, Pat. No. 5,605,831.
[51] Int. Cl.[6] .................................................. A61K 39/395
[52] U.S. Cl. ........................ 435/7.23; 435/240.27; 530/387.9; 436/512
[58] Field of Search ................... 424/178.1; 435/240.27; 530/387.9; 436/512

[56] References Cited

U.S. PATENT DOCUMENTS 4,590,071  5/1986  Scannon et al. .

OTHER PUBLICATIONS

Gown, et al., *The American J. Pathology* (1986) 123:195–203.
Sevier et al. Clinal Chemistry 27/11: 1797–1806, 1981.
Wittbrodt et al. Nature 341:415–421 1989.
Parker et al. Biochemistry 25, 5425–5432, 1986.
Lerner, T. Nature, 299: 592–596, 1982.
Staerz, et al. PNAS. 83: 1453, 1986.
Waldman, W. Science, 252: 1657–1662, 1991.
Real et al. Cancer Res. 46: 4726–4731, 1986.
Carrasquillo et al. Cancer Treatment Reports 68: 317, 1984.
Hird, et al. Genes & Cancer, pp. 183–189 1990.

*Primary Examiner*—Lila Feisee
*Assistant Examiner*—Minh-Tam B. Davis
*Attorney, Agent, or Firm*—Rae-Venter Law Group P.C.

[57] ABSTRACT

Methods and compositions are provided for detecting antigens having a specific epitope associated with melanoma and prostatic carcinoma. The epitope is present in melanoma cells and prostatic cancer cells but is essentially absent from melanocytes and normal prostatic tissue. The antibody can be used in diagnostic methods for histochemical detection of human melanoma and prostate carcinoma, of various progression stages and in treatment of melanoma and prostate carcinoma.

12 Claims, 3 Drawing Sheets

(1 of 3 Drawing Sheets in Color)

MELANOMA AND PROSTATE CANCER SPECIFIC ANTIBODIES FOR IMMUNODETECTION AND IMMUNOTHERAPY

CROSS-REFERENCE TO RELATED APPLICATION

This application is a continuation-in-part of U.S. Ser. No. 07/829,855 filed Jan. 31, 1992 U.S. Pat. No. 5,605,831 which disclosure is herein incorporated by reference.

INTRODUCTION

1. Field of Invention

The subject invention is related to the use of antibodies, which bind to a unique peptide obtainable from Xiphophorus melanoma mrk-receptor tyrosine kinases. The methods are exemplified by use of the antibodies for the diagnosis and therapy of melanoma and prostate cancer.

2. Background

Human malignant melanoma arises from a series of stages starting with the harmless mole, going through intermediate stages of radial to invasive growth and ending in the destructive final stage of metastatic melanoma. Melanoma usually resists chemotherapy as well as radiotherapy. Surgery is the most effective treatment. However, for it to be effective, surgery requires early diagnosis which is unfortunately hampered by the lack of accurate markers for melanoma. Melanoma associated antigens have been found, but they are of little diagnostic value. For example, the nerve growth factor receptor is found in high density on melanoma cells. However, monoclonal anti-nerve growth receptor antibodies are specific for neural crest cell diseases rather than for melanoma alone. Likewise, other melanoma associated antigens against which antibodies have been raised are nonspecific for melanoma cells. Examples are the monoclonal antibodies raised against in vitro grown melanoma cells which are directed against gangliosides or glycoproteins present on the melanoma cells. Both antigens are also found on other cells. It is therefore of interest to identify a melanoma-associated antigen which is specific for melanoma as compared to normal melanocytes as well as other normal and malignant cells. An antibody raised against such an antigen could be used in the diagnosis and treatment of melanoma. Adenocarcinoma of the prostate is one of the most common tumors in men and accounts for 10% of deaths from malignant disease in males in the United States. Only a small proportion of these cases becomes clinically apparent prior to death, the remainder being latent carcinoma. Three-fourths of the tumors arise in the posterior lobe, and urinary symptoms therefore tend to occur late in the disease. Frequent routine rectal examinations are the best means of demonstrating the early and operable tumors. Measurement of prostate specific antigen as a screening test for prostate cancer has been used but presents both technical difficulties and a high false positive rate. Prostatic acid phosphatase also has been used as a marker for prostate cancer but does not detect all cancers. Currently the most successful detection of prostate cancer is from the combined use of a digital rectal exam, transrectal ultrasound and detection of prostate specific antigen. Sensitivities of the three tests individually vary from 50% to 85% but the positive predictive value fluctuates around 30%. When these three investigations are summated, the detection rate is approximately twice as high as when a single parameter is used. However, currently the only reliable procedure for definitive diagnosis is by open perineal biopsy. A significant number of patients come into the physician with symptoms due to distant metastases. Needle biopsies and cytologic studies of prostatic fluid are unreliable for the diagnosis of early cancer but are useful methods of obtaining a histological diagnosis in the more advanced cases. Radical prostatectomy remains the treatment of choice for tumors confined to the gland but this is applicable to only a tiny fraction of cases. Orchiectomy and hormone therapy (usually estrogen therapy) together appear to be the most effective palliative treatment in patients with symptomatic cancer of the prostate and are also used as an adjunct to surgery. However, there are significant side effects to the use of estrogens, including an increase in mortality from cardiovascular disease. It therefore is of interest to identify in particular, early stage prostatic cancer and to identify non-invasive methods of treating prostatic cancer.

Relevant Literature

U.S. Pat. No. 4,590,071 is directed to a cytotoxic conjugate specific for human melanoma. Maguire, et al., *Cancer* (1993) 72:(11 Suppl.) 3453–62, disclose use of an antigen expressed by the majority of adenocarcinoma for preparation of immunoscintigraphic agents for the preclinical staging of prostatic carcinoma in patients with negative or equivocal results on standard imaging tests. Lopes, et al., *Cancer Research* (1990) 50:6423–9, disclose a prostate-reactive monoclonal antibody. Horoszewicz (U.S. Pat. No. 5,162,504), discloses monoclonal antibodies to an antigen on prostatic epithelial cells.

SUMMARY OF THE INVENTION

The present invention provides methods and compositions useful for detecting or monitoring primary and metastatic carcinomas which contain an epitope on their surface which reacts with an antibody produced using an immunogen comprising a unique sequence derived from a Xyphophorus melanoma. The method relies on the detection of the epitope on carcinoma cells which is specific for the carcinoma cells, particularly melanoma and prostate carcinoma cells. The epitope can be detected on the carcinoma cells in tissue biopsies, in carcinoma cells in culture, as well as in blood samples. The antigen appears to be located on the surface of the carcinoma cells and may be a cell surface receptor. The putative receptor has an apparent molecular mass ($M_r$) of 170,000 by western blotting of lysates of a melanoma cell line. Detection of the epitope conveniently is accomplished by reaction with monoclonal antibodies derived from hybridoma cell line 12f3.2, or antibodies having a similar specificity, and determining the formation of specific antigen-antibody complexes. The antigens and/or antibodies find use in vitro or in vivo in diagnosis and therapy. Antiidiotypic antibodies and the antigenic peptide also find use for detecting the presence of antibodies to the antigen in the blood or serum of a human host.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 1. (a) Schematic structure of putative mrk receptor tyrosine kinase, SP=signal peptide, TM=transmembrane domain, TK=tyrosine kinase domain, striped boxes=cystine-rich domains, below similarities of various domains to the human epidermal growth factor receptor HER-1 (our own and data from Wittbrodt, et al., 1989); (b) surface values of amino acid residues 340–640 in which the peptide spans amino acids 480–489 (marked in yellow); (c) nucleotide sequence and amino acid sequence (below) spanning the amino acid sequence from 446–486.

DESCRIPTION OF SPECIFIC EMBODIMENTS

Methods and compositions are provided for the detection, identification, monitoring and treatment of carcinomas, especially melanomas and prostatic tumors, including high grade prostatic intraepithelial neoplasia (PIN). In melanomas, an about 180 KD protein is present on the cell surface of the melanoma cell which is immunologically related to an mrk-receptor tyrosine kinase present in the Xiphophorus fish melanoma. Thus, patient samples may be screened for melanoma by assaying for the presence of this cell surface protein in patient samples, including tissue biopsy specimens and blood samples; the receptor apparently is "shed" into the bloodstream. Unexpectedly, the antibody has now been shown to recognize PIN which gives rise to malignant prostatic cancer cells as well as prostate cancer. The antibody shows no cross-reactivity with normal tissues, either melanocytes or prostatic tissue.

The Xiphophorus fish melanoma model is well established as a model for human malignant melanoma. In both, the melanomas are made up of the same cell type and are of the same developmental origin, the neural crest. The stages of melanoma progression which have been characterized for melanomas in humans are similar to those found in fish. One particular type of human melanoma, familial subcutaneous malignant melanoma is clustered in families, thereby indicating a genetic basis. Genes identified in the fish as being relevant to pigment cell development and/or melanoma formation can therefore be used as probes to isolate the human counterpart from genomic or cDNA libraries. Genes also can be used in raising antibodies against antigens found on human melanoma cells.

The Xiphophorus fish melanoma model is well established as a model for human malignant melanoma. Several genetic factors can be identified which mediate the progression of a normal melanin-bearing pigment cell into a malignant, metastatic melanoma cell. One complex locus encompasses genetic information for the formation and location of macromelanophores and also for melanoma permissiveness; the term "macromelanophore" refers to the large melanophores found in Xiphophorus which are larger and have more melanin pigment than melanocytes in the human. To identify oncogene related genes on the chromosome carrying the complex locus, the Xiphophorus fish genome can be screened with conserved oncogene probes. Genetic linkage analysis is then used to identify genes which are closely linked to the complex locus and thus a candidate for any of the encoded information in the complex locus, for example, for melanoma permissiveness, and then to differentially screen for those genes found only in cells which produce the pigment cell giving rise to melanomas. Examples of such genes are the erb-B related gene, and the src (Rous sarcoma virus) oncogene. Genomic and cDNA clones were isolated and partially sequenced; and RNA expression studies carried out to identify genes which are preferentially expressed in tissue containing melanophores and which are highly expressed in the fish melanomas. Using this methodology genes which are specific for melanomatosis pigment cell growth can be identified. The gene product, or a portion thereof then is used to generate monoclonal antibodies. In order to obtain a highly specific antibody, the deduced amino acids encoded by the gene can be evaluated to identify a portion of the expression product most likely to be highly antigenic such as the extracellular domain of a surface receptor.

The sequence also can be evaluated to identify a unique amino acid sequence, i.e., a portion of the polypeptide which is not found in other proteins using data bank comparisons and computer modeling. A peptide containing the amino acid sequence and optionally any additional residues desirable for coupling to a carrier for immunization is then prepared. The oligopeptides combine the desired amino acid sequences in substantially pure form. Thus, usually the subject composition is at least 80 mole percent, usually at least about 90 mole percent of the particular oligopeptide or mixture of oligopeptides which come within a particular formula.

The subject compounds are made in conventional ways which can be employed for the production of oligopeptides. Techniques include using automatic peptide synthesizers, employing commercially available protected amino acids. Alternatively, recombinant DNA technology may be employed, by synthesizing according to conventional procedures the appropriate nucleotide sequence, joining the sequence to an appropriate replication vector, transforming a post cell and cloning and growing the transformed host cell to produce the oligopeptides of interest which may then be isolated.

For preparation of antibodies, the subject compounds are conjugated to an immunogenic carrier, for example antigen proteins, to act as a hapten for production of antibodies specific for an epitope on melanoma or prostatic carcinoma cells. Various proteins are employed as antigens which are not endogenous to the host. Commonly employed antigens are the albumins, globulins, keyhole limpet hemocyanin, or the like. Haptenic conjugates to antigens are well known in the literature under and are amply exemplified in a wide variety of patents. See for example, U.S. Pat. Nos. 4,156,081, 4,069,105 and 4,043,989.

The haptenic antigen conjugates are used in accordance with conventional ways to immunize a mammal, for example, rat, mouse or higher mammal, for example, primate, including human in accordance with conventional procedures. See, for example, U.S. Pat. Nos. 4,172,124, 4,350,683, 4,361,549, and 4,464,465. Hybridomas are prepared by fusing available established myeloma lines, for example, SP2-0, NS/1, AG8.6.5.3, etc. with peripheral blood lymphocytes, for example, splenocytes or other lymphocytes of the immunized host. The resulting immortalized B-lymphocytes, for example hybridomas, heteromyelomas, EBV transformed cells etc., are then selected, cloned and screened for binding to the subject epitope.

The antibodies obtained and employed may be any one of the classes, such as IgA, IgD, IgE, IgG and IgM, and any one of the subclasses of the various classes. In addition, whole antibodies or fragments of the antibodies may be employed, such as FAB, F(ab)'$_2$, F$_v$, or the like. The subject immortalized B-lymphocytes or other cells, for example T-cells, which provide receptors specific for the subject epitope, can be used as a source of DNA, either genomic or cDNA, for expression of the ligand heavy chains of the receptors in procaryotes or eucaryotes. The resulting products may then be used as receptors for binding to the subject epitopes.

The epitopes are characterized as being present on melanoma cells and essentially absent from normal melanocytes. The antigen binds specifically to the monoclonal antibody 12f3.2 and has an apparent relative molecular mass of about 170,000 in the PSM cell line. Once antibodies are available which are specific for the epitope, the antibody can be used for screening for different antibodies from the same or a different host which bind to the same epitope by employing the subject antibody 12f3.2 or antibodies prepared to the epitope which cross-react with 12f3.2. Monoclonal antibody 12f3.2 is secreted by hybridoma cell line 12f3.2. The hybridoma cell line 12f3.2 was deposited with the American Type Culture Collection ("ATCC"), 12301 Parklawn Drive, Rockville, Md. 20852, on Jan. 27, 1993, under ATCC Accession No. HB11252.

The antibodies find use in diagnosis, with tissue employing cytology, with lysates of tissue or in detecting the subject epitope in blood or serum. A wide variety of techniques and protocols exist for detecting an antigen in a sample suspected of containing the antigen. Protocols involve a wide variety of labels, which labels include radio-nuclids, enzymes, fluorescers, fluorescer-quencher combinations, chemiluminescers, magnetic particles, radiopaque dyes, and the like. These labels can be directly conjugated to the monoclonal antibody through a variety of covalently bonded linking groups and functionalities. Some of the techniques involve having one of the members of the antigen-antibody complex bound to a support, such as a particle or vessel wall, while other of the assays are performed in solution without a separation step, where uncomplexed label is separated from complexed label. In a number of assays, the antibody need not be labeled, such as in hemagglutination or where anti-immunoglobulin is employed and the anti-immunoglobulin is labeled, so as to provide for indirect labeling of the subject monoclonal antibody. Assays which can be employed includes assays such as ELISA, RIA, EIA, PCR (Frye, et al., Oncogene 4:1153–1157, 1987) and the like.

Generally, it is necessary to pretreat the tissue sample in some manner prior to performing a screening assay, generally immunoassay. Sample preparation will vary depending on the source of the biological sample. Cell or tumors and other tissue samples may be prepared by lysing the cells. Serum samples typically can be prepared by clotting whole blood and isolating the supernatant in accordance with well known methods.

For diagnosis of melanoma, PIN or prostatic carcinoma, biopsy specimens are the most likely source of samples for analysis. Conventional immunohistochemical staining techniques also can be used for detecting the epitope in tissue samples. For example, the tissue sample may be fixed in formalin or other standard histological preservatives, dehydrated and embedded in paraffin as is routine in any hospital pathology laboratory. Sections can be cut from the paraffin embedded material and mounted on glass slides or the sections can be prepared from cryo-preserved tissue. Alternatively, cytological preparations can be used. For example, cells from the tissue sample can be fixed on a slide, typically by exposure to formalin in a buffer at physiologic pH, followed by suspension in acetone and pelleting onto gelatin-coated slides by centrifugation. The cellular antigen can be localized, either by exposure to labeled antibody or by exposure to unlabeled antibody and a labeled secondary antibody. The amount of the cell surface protein or antigen in the sample is directly proportional to the amount of bound label.

Whole body imaging techniques employing radioisotope labels can be used for locating melanomas, or prostatic carcinoma, both primary tumors and tumors which have metastasized. The antibodies of the present invention, or fragments thereof having the same epitope specificity, are bound to a suitable radioisotope, typically technetium-99, $^{123}$iodine, $^{125}$iodine, or $^{131}$iodine, or a combination thereof, and administered parenterally. For prostatic cancer, administration preferably is intravenous. High specific activity labelling of antibodies or fragments with technetium-99m is described for example in U.S. Pat. No. 5,317,091, U.S. Pat. No. 4,478,815, U.S. Pat. No. 4,478,818, U.S. Pat. No. 4,472,371, U.S. Re. 32,417, and U.S. Pat. No. 4,311,688. The bio-distribution of the label is monitored by scintigraphy, and accumulations of the label are related to the presence of melanoma cells or prostate cancer cells. Whole body imaging techniques are described in U.S. Pat. Nos. 4,036,945 and 4,311,688. The disclosures of the cited patents are incorporated herein by reference. Other examples of agents useful for diagnosis and therapeutic use which can be coupled to antibodies and antibody fragments include metallothionein and fragments (see, U.S. Pat. No. 4,732,864).

Monoclonal antibodies can be used in other ways than binding to the subject epitopic site. Monoclonal antibodies to the epitopic site may in turn be used as antigens for the production of monoclonal antibodies specific for the idiotypic side of the monoclonal antibody to the cell surface receptor, for example 12f3.2. The anti-idiotypic monoclonal antibody can be used to detect the presence of antibodies in a host to the cell surface receptor, where the monoclonal antibody to the cell surface receptor and the physiological fluid to be diagnosed are from the same host. For example, where the monoclonal antibody to the cell surface receptor is a human antibody or a humanized antibody, then the monoclonal antibody to the cell surface receptor can be used as an antigen to make monoclonal antibody specific for the human idiotype for the cell surface receptor, which monoclonal antibodies can be used to detect antibodies to the cell surface receptor which are present in a human physiological fluid, for example blood or serum. The anti-idiotypic monoclonal antibody can be made in any host, for example rodent, more particularly rat or mouse.

In addition, the conformation of the idiotype of the anti-idiotypic monoclonal antibody resembles the epitope of the cell surface receptor and thus can serve as an antigen in competition with the cell surface receptor epitope. To that extent, the idiotypic monoclonal antibody can serve as a vaccine in inducing an immune response to the cell surface receptor epitope different from the immune response obtained with the cell surface receptor. Furthermore, the anti-idiotypic monoclonal antibody can serve as a reagent as a ligand which is competitive with the cell surface receptor. The monoclonal antibodies also can be used as a means of purifying the cell surface receptor from melanoma cells and prostatic cancer cells, for example in combination with a solid support, to form an affinity matrix.

The specificity of the monoclonal antibodies makes them useful as targeting agents for human melanoma cells or prostatic cancer cells. For example, the antibody can be coupled to a cytotoxic agent using methods known to those skilled in the art. For example, see U.S. Pat. No. 4,590,071 and U.S. Pat. No. 5,055,291, which disclosures are incorporated herein by reference. T-cell therapy also may be used, for example, see Rosenberg, *New England Journal of Medicine* 316: 789, 1987, which disclosure is incorporated herein by reference.

The following examples are offered by way of illustration and not by way of limitation.

EXAMPLES

Example 1

Preparation of Melanoma-Specific Antigen

The Xiphophorus fish genome was screened with conserved oncogene probes to identify oncogene-related genes on the chromosome carrying the complex locus which encompasses genetic information for the formation and location of macromelanophores and melanoma permissiveness. To isolate the genes of the major loci, oncogene probes were used to identify restriction fragment polymorphisms (RFLPs) as markers for these loci. RFLPs were found for genes similar to the src and the erb-B genes (Vielkind and Dippel, *Canadian Journal of Genetics and Cytology*, Vol. 26:607–614 (1984)). The latter gene appears to be closely linked to the sex-linked pigmentary locus and is considered to be a candidate gene for some of the information contained in this locus.

Using the erb-B oncogene probe, a genomic phage library was screened and several positive clones were isolated. The clones were characterized by restriction enzyme mapping, which yielded five clones that encompassed the same restriction fragments as those identified in genomic southern blots using the erb-B probe. Probes from these Xiphophorus clones were used to screen two cDNA libraries yielding twenty clones, one of which carried an insert corresponding to the RNA fragment detected in a Northern blot analysis of the RNA from the PSM cell line. Restriction mapping of this clone as well as partial sequencing revealed that the identified gene is probably identical to the published Xmrk gene (Wittbrodt et al., 1989, *Nature* 341:415–421).

Differential PCR analysis with total RNA from testis, ovary, liver, kidney, brain, eye, skin, skin areas with melanophores, and melanomas using mrk-specific primers revealed that mrk is preferentially expressed in tissue containing melanophores and is highly expressed in the melanomas. This and the fact that this gene is found only in fish that can produce the cells giving rise to melanoma make it a specific gene for melanomatosis pigment cell growth.

Comparisons of the mrk sequence were done with sequences contained in the latest available Genebank and EMBL Genebank computer programs and its deduced amino acid sequence showed that the putative protein belongs to the family of receptor-tyrosine kinases which include an extracellular domain, a transmembrane domain and a cytoplasmic tyrosine kinase domain; the protein is most closely related to the human epidermal growth factor receptor (FIG. 1) but contains unique sequences not present in the epidermal growth factor receptor. The cytoplasmic tyrosine kinase domains are highly conserved domains and the transmembrane domain is unlikely to be highly antigenic. Therefore, the extracellular domain was further evaluated to find a portion of that domain which is not found in other proteins such as the epidermal factor receptor protein and for which high antigenicity can be assumed.

Figure 1A:
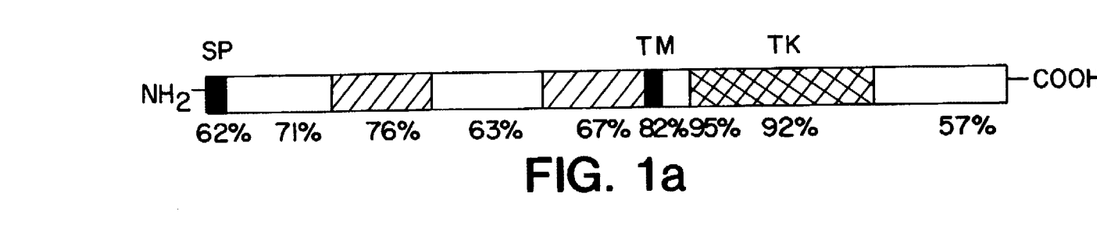
Figure 1B:
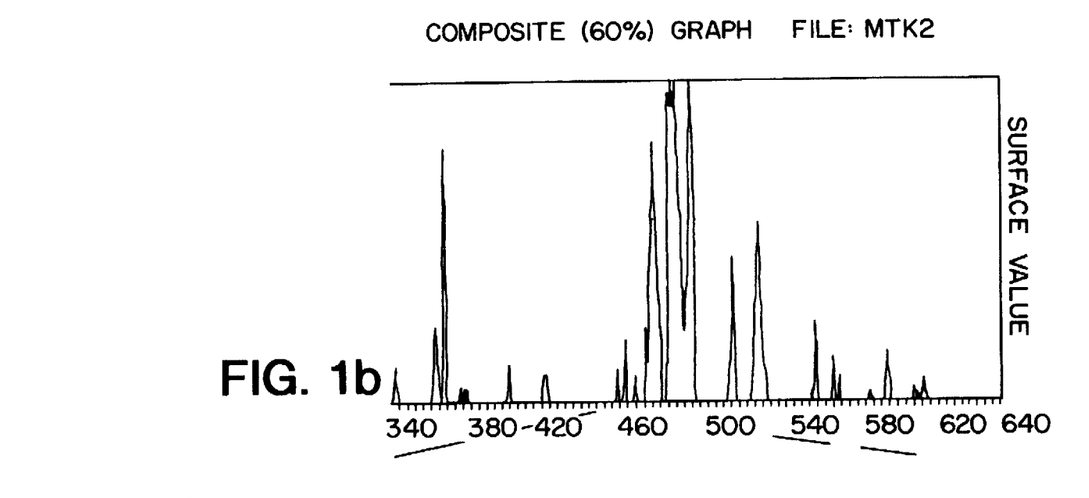
Figure 1C:
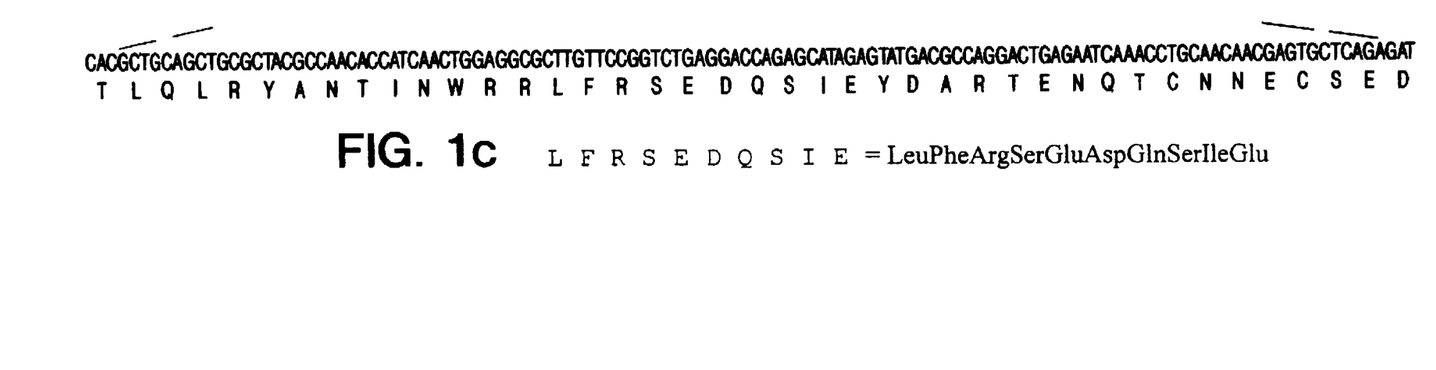

A computer modeling (Surfaceplot-Synthetic Peptides, Inc.; see Parker et al., *Biochem* 25:5426–5432, 1985) of the putative mrk-receptor protein was done to predict the antigenicity of portions of this protein. An exposed sequence of 10 amino acids (L-F-R-S-E-D-Q-S-I-E) (SEQ ID NO:1) of the extracellular domain met this demand. The amino acid sequence of this portion of the mrk-protein also avoids any similarity to the amino acid sequences of the true epidermal growth factor receptor of fish or human origin and according to an extensive search in the gene/protein data banks, no significantly similar amino acid sequences exist in other proteins. This sequence, therefore, appears to be rather specific for the novel receptor; a peptide was therefore synthesized and used for the generation of antibodies (FIG. 1). For coupling to the hapten, the peptide was synthesized with a cysteine residue at the N-terminus. The peptide was coupled to the hapten KLH (keyhole limpet hemocyanin, Pierce Chemical Co.), via SMCC (succinimidyl 4-(N-malemido-methyl)cyclohexane-1 carboxylate, Pierce Chemical Co.) (see Sutcliffe et al., 1980; Sela, Synthetic Vaccines Vol. 1 R. Arnon (Ed.), CRC Press, Boca Raton, Fla., pp. 85–92, 1987).

Example 2

Preparation of Antibodies to Mrk-receptor Protein Fragment

Immunization

The hapten-peptide conjugate was mixed 1:1 with Freund's complete adjuvant and 0.8 ml injected intraperitoneally (ip) into each of three Fischer rats (125–150 g body weight) at a concentration of 0.5 mg/ml. After 14 days, a second ip injection of the KLH-peptide conjugate was given, and then 4 times at 14 day intervals the uncoupled peptide at a concentration of 0.5 mg/ml was injected. At that time, a positive immunoresponse of the serum of the rats was identified by standard ELISA methodology using cells from the Xiphophorus fish melanoma cell line (PSM line) which show a high expression of the mrk gene as positive and the Xiphophorus fibroblastoid cell line (XGI line) as negative control as was the rat preimmune serum; staining was done using goat anti-rat IgG (H+L) (Jackson Immun. Lab.) as secondary antibody conjugated to horseradish peroxidase and OPD (o-phenylenediamine dihydrochloride, Sigma) as the chromogenic substrate. Another ip immunization with the peptide at a higher concentration (0.8 mg/ml) then was done followed by an intravenous injection of the peptide (0.8 mg/ml) without Freund's adjuvant 3 weeks later. Four days later monoclonal antibody production was started by fusing $4\times10^8$ spleenocytes from the rat which gave the strongest immunoresponse to $0.8\times10^8$ SP2/O mouse myeloma cells. Fourteen 96-well microtitre plates were seeded with a spleen cell density of $1.25\times10^3$ cells/well. Cells were grown for 7 days in HAT-DMEM (TFL Media Preparation Service, Vancouver, B.C.) supplemented with 50 µ/ml of Interleukin-8.

Isolation of Clones

Screening of monoclonal producing hybridoma cells was done on terazaki plates coated with cells fixed in 0.05% glutaraldehyde from the PSM melanoma cell line as positive control and as negative controls with cells from the XGI cell line, from a gonadal cell line of trout, with fibroblasts and bone marrow cells from human; staining was done as noted above. Cells from 28 wells which yielded a positive signal with the PSM cells were transferred from the microliter plates into 1 ml of HT-DMEM in 24-well plates and after 3–6 days plated in methylcellulose. Isolation of individual pure hybridoma clones was done by picking at least 12 individual colonies derived from the original positive cells, transferring them into 96-well microliter plates and testing again for positive reactivity with the PSM cells and also with the peptide; as negative controls the cells mentioned above were also tested. Three clones were isolated which produced monoclonal antibodies that reacted positively with the peptide and the fish melanoma cell line but exhibited no reactivity with the other cells.

Two other clones, 10A3 and 3B7 reacted less strongly and three clones, 5C1, 6E4, and 14C7, reacted not only with the peptide and the fish melanoma cell line but also with a trout cell line, making them more general.

Typing of Antibody

Supernatants of the three positive hybridoma clones were subsequently reacted with cultured PSM as well as XGI cells fixed on the culture dishes with 4% paraformaldehyde (20 min, RT); staining was done using anti-rat 2nd-Ab conjugated to horseradish peroxidase (Jackson Immun. Lab.) and DAB (3,3'-diaminobenzidine, Sigma) as chromogenic substrate or with goat anti-rat F(ab)$_2$ FITC-coupled secondary Ab (Cappel). The clone 12f3.2 produced the strongest signal with the PSM cells and we thus concentrated on it first. Typing of this mAb using a Bio-Rad kit which is a mouse typing kit but also has cross-reactivity with rat Abs revealed that the mAb of the hybridoma clone 12f3.2 is an IgG$_1$(k).

Immunostaining of Cells from Xiphophorus PSM Melanoma Cell Line

To further verify the specificity and identify the location of the antigen recognized by the peptide-specific mAb, cultured cells of the PSM cell line were fixed and stained (see above) with supernatants of the mAb producing clone 12f3.2. The PSM line contains all stages of pigment cell differentiaton; spindle-shaped premelanocytes, young melanocytes with fine few dendrites, polydendritic adult melanocytes, and finally also the large melanophores with broad dendrites which are fully loaded with brown-black melanin pigment. Staining however, was found only in the younger stages, the melanocytes, at the contact sites of their dendrites, on the edges concentrated in spots and in areas where the cells narrow towards the dendrites. This staining pattern is typical for a cell surface receptor or cell contact type antigen. This is in keeping with data we have deduced from the nucleotide sequence, i.e. that the putative mrk protein is a cell surface receptor. This staining behavior is more prominent in vitally stained cells and using the FITC-coupled 2nd anti-rat IgG antibody.

Example 3

Characterization of Antibody Specificity for Melanoma Tissue mAb Reacts with Pigment Cells from Normal and Melanoma Tissue in Xiphophorus While the culturing of melanoma cells can yield valuable information, the classification of the disease state must be done on sectioned material. In order to test the suitability of the produced mAb 12f3.2, cross-sections from frozen as well as paraffin embedded material were stained using the avidin-biotin procedure (ABC staining kit, Vector Lab.) and AEC (3-amino-9 -ethylcarbazole, Sigma) as chromogenic substrate. So far we have obtained with mAb 12f3.2 supernatant (1/50 in PBS) a positive signal in frozen positioned and acetone-fixed Xiphophorus dorsal fin material which contains in the dermis fully differentiated melanophores and immature, non-pigmented precursors underlying the differentiated cells. Interestingly, staining was not observed in the melanophores but in the precursors. Sections of melanoma tissue stained positive in areas representing tumor growth and in areas which are composed of spindle-shaped, lightly pigmented cells.

mAb Stains Human Melanoma Cells But Not Normal Melanocytes In Vitro

The encouraging results of the detection of melanoma cells from our model led us to further test the mAb by immunostaining human melanoma cell lines derived from patients from whom B-cells were also available as a control. The cells in the culture dishes were fixed with 0.4% paraformaldehyde for 30 min. at RT and then immunostained as described above for cultured fish cells. All three melanoma cell lines KZ-2,-13,-28 stained positively but each in a characteristic way. The spindle-shaped, dendritic KZ-2 cells exhibited an evenly distributed staining with some spots of more concentrated staining, the dendritic to polydendritic KZ-13 cells exhibited the staining in the cell's body and at the start of the dendrite, and the larger KZ-26 cells which have broad dendrites and tend to conglomerate show strong staining in the centers of these concentrations presumably where their dendrites contact each other. The B-cells of the patients did not show any staining at all nor did the cultured melanocytes derived from human foreskin. The history of the human melanoma cells are not quite clear with regard to classification of the described stages above, i.e. radial, vertical growth phase, metastatic phase. However, the KZ-2 cells show the fastest, KZ-13 slower and the KZ-26 cells an even slower growth. Thus, the mAb appears to yield a characteristic staining of melanoma cells of various growth potentials.

mAb Reacts with Human Melanoma Tissue

The most important question to answer was whether or not the mAb specifically recognizes human melanoma tissue. Sections from three primary and four metastatic acetone-fixed and paraffin-embedded human melanoma specimens obtained from six different patients were stained with the mAb 12f3.2 supernatant diluted 1/50 with PBS as described above for the sections of fish tissue; all melanomas showed positive staining. In the primary melanomas, nests of stained (positive) melanoma cells were observed while in the metastatic tumors the positive cells were more dispersed; two of the metastatic tumors of the same patient showed strong staining that appeared as grainy spots indicative of antigen located on the surface of the melanoma cells. The healthy skin, including melanocytes and other cell types within the melanoma, e.g. lymphocytes, did not show any staining.

Identification of Melanoma Related Characteristics by Western Blotting

Another possibility to identify melanoma specificity is to analyze electrophoretically separated proteins on nitrocellulose blots. Therefore cells of the PSM and KZ melanoma cell lines were lysed and separated and blotted according to standard conditions and the blots immunostained with the mAb. Only the melanoma showed a positive signal; the PSM cells revealed a weak signal at 170,000 $M_r$ which would be expected from the predicted amino acid sequence and a strong signal of approx. 60,000 $M_r$ which may be a degradation product of the activation and signal transduction of the mrk-receptor tyrosine kinase (see Ullrich and Schlessinger, Cell 61:203–212, 1990). Signals in very similar size ranges were detected in the human melanoma cells. No signal at all was found in lysates derived from the control XGI cell line, which is to be expected as these cells do not express the mrk gene.

A rat monoclonal antibody was produced against a synthetic peptide which represents a putative highly antigenic portion of a novel receptor tyrosine kinase protein. The protein is coded by a melanoma pigment cell specific gene which was cloned from Xiphophorus fish. Xiphophorus represents an animal melanoma model which is well established as a model for human melanoma formation.

The mAb recognizes the prepigment cells in situ, the undifferentiated melanocytes of a Xiphophorus melanoma cell line and also the melanoma cells in growth areas of Xiphophorus melanomas. It also reacts characteristically with cultured human melanoma cells of different growth potentials and with primary and metastatic secondary melanomas in situ. The staining pattern of secondary melanoma cells has a grainy appearance. The mAb does not react with normal human cultured melanocytes nor with those that are located in the normal skin adjacent to the melanomas. In conclusion, the mAb can be used as a tool for histochemical characterization of melanoma cells in patients for immunodiagnosis of both primary and metastic melanomas, and for treatment of melanomas by immunotherapy.

Example 4

Specificity of Antibody 12f3.2 for Prostate Cancer

This study was performed to determine whether the antibody directed to a peptide have the amino acid sequence depicted in SEQ ID NO.:1 may also be specific for cancer of the prostate and high grade prostatic intraepithelial neoplasia (PIN) which gives rise to malignant cancer cells. Forty-seven biopsies from radical prostatectomies, which fulfilled the criterion that no treatment prior to the operation was given to the patient which could otherwise cause antibody reactivity, were immunostained using the methods described in Example 3. The data are summarized in Tables 1 and 2 below.

TABLE 1

XMEL Immunohistochemical reactivity in biopsies from radical prostatectomies and samples from normal tissues

| Block # | % of pos. cancer cells | Intensity | PIN | Normal gland | Control |
|---|---|---|---|---|---|
| 95-1 | 100 | 3+–4+ | absent | — | all neg |
| 95-2 | 2 | 1+–2+ | in all | — | |
| 95-3 | 60 | 3+–4+ | samples | — | |
| 95-4 | 60 | 3+–4+ | | — | |
| 95-5 | 50 | 3+–4+ | | — | |
| 95-6 | 95 | 4+ | | — | |
| 95-7 | 70 | 3+ | | — | |
| 95-8 | 2 | 1+ | | — | |
| 95-9 | 2 | 2+ | | — | |
| 95-10 | 2 | 2+–3+ | | — | |
| 95-11 | 40 | 2+–3+ | | — | |
| 95-12 | 5 | 1+ | | — | |

| Block # | Type | XMEL Reactivity | Control |
|---|---|---|---|
| 95-13 | normal prost | neg | all neg |
| 95-14 | sem vesicle | neg | |
| 95-15 | normal liver | neg | |
| 95-16 | muscle | neg | |
| 95-17 | kidney | neg | |
| 95-18 | lung | neg | |
| 95-19 | colon | neg | |
| 95-20 | skin | neg | |

— = absent; 1+ = weak; 2+ = moderate; 3+ = strong; 4+ = very strong; neg = negative
PIN = high grade 3 prostatic intraepithelial neoplasia, control = no primary antibody added

TABLE 2

XMEL Immunohistochemical reactivity in biopsies from radical prostatectomies from a cohort of cancer patients studied in 1985–1987

| Case | % of pos. cancer cells | Intensity | Normal gland | PIN | Control | Comments |
|---|---|---|---|---|---|---|
| 85-1 | 0 | — | neg | | all neg | |
| 85-2 | 0 | — | neg | | | |
| 85-3 | 10 | 1+ | neg | | | |
| 85-4 | 0 | — | neg | 1+ | | |
| 85-5 | 0 | — | neg | 1+ | | |
| 85-6 | 0 | — | neg | | | |
| 85-7 | no cancer | — | neg | 1+ | | |
| 85-8 | 0 | — | neg | | | |
| 85-9 | 0 | — | neg | | | |
| 85-10 | 10 | 1+ | neg | | | |
| 85-11 | 0 | — | neg | | | |
| 85-12 | 0 | — | neg | 1+ | | |
| 85-13 | 0 | — | neg | 1+ | | |
| 85-14 | 0 | — | neg | | | |
| 86-1 | 0 | — | neg | 1+ | | |
| 87-1 | 30 | 1+ | neg | | | |
| 87-2 | 10 | 1+ | 1+ | 1+ | | |
| 87-3 | 20 | 1+ | neg | 1+ | | |
| 87-4 | 30 | 1+ | neg | 1+ | | |
| 87-5 | 40 | 1+ | neg | 3+ | | |
| 87-6 | 5 | 1+ | neg | 1+ | | |
| 87-7 | 0 | — | neg | | | |

— = absent; 1+ = weak; 2+ = moderate; 3+ = strong; neg = negative
PIN = high grade 3 prostatic intraepithelial neoplasia, control = no primary antibody added In Table 1 we have additionally included results from normal tissue samples, because for a possible immunotherapy with this antibody it is necessary to establish that the antibody shows no cross-reactivity with normal tissues of the patient. As can be seen from Table 1, all prostate cancers stain positive with the antibody although with various intensities and variable numbers of the cancer cells, while the normal gland component was negative as were the normal tissues including the sections from non-cancerous, normal prostate. The data shown in Table 2 pertain also the question of specificity but represent the initial data on the question of prognosis. These samples were chosen from a cohort of patients from whom tissue blocks had been obtained and stored for several years. The reactivity with these biopsies is less strong, which most likely is due to the fact that these are sections from paraffin blocks which are more than 10 years old and which usually yield a less strong immunosignal. The fact that 14/22 cancer and/or PIN samples stained positive shows that the antibody is specific for the malignant stages of carcinoma of the prostate.

In accordance with the subject invention, antibodies and their complementary antigens are provided which bind specifically to human melanoma and human prostatic cancer cells. The antigens are believed to be cell surface receptors, related to a mrk-receptor tyrosine kinase, where the whole mrk-receptor or fragments thereof, including the epitopic site of interest, can be employed by themselves or in conjunction with complementary antibodies as reagents in diagnostic assays. In addition, the antibodies find use in in vivo imaging and therapy. The antibodies can also be used in such homology of biopsy specimens with the detection of the presence of the antigen and the tissue. The presence of the tumor marker found in the blood is indicative of the existence of a melanoma or prostatic carcinoma. Thus, not only is it feasible to detect at an early stage the existence of melanoma cells and prostatic carcinoma cells in a human host, but further, to detect their specific location in the human host. In addition, antibodies to the antigen are indicative of the existence of melanoma or prostatic carcinoma, primary or metastic, or its recurrence.

All publications including patent applications mentioned in this specification are indicative of the level of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be apparent to one of ordinary skill in the art that many changes in modifications can be made thereto without departing from the spirit or scope of the appended claims.

What is claimed is:

1. A method for detecting the presence of melanoma or prostatic cancer in a human host, said method comprising:
   combining a sample from said human host with antibodies which bind specifically to a peptide having the amino acid sequence depicted in SEQ ID NO:1 and detecting formation of immune complexes as indicative of the presence of melanoma cells or prostatic cancer cells.

2. The method according to claim 1, wherein said sample is a tissue sample.

3. The method according to claim 2, wherein said tissue sample is paraffin-embedded or cryo-preserved.

4. The method according to claim 1, wherein said antibodies are monoclonal antibodies.

5. The method according to claim 4, wherein said monoclonal antibodies or second antibodies to said monoclonal antibodies are conjugated to a label which provides a detectable signal.

6. The method according to claim 5, wherein said label is a radionuclide, a fluorescer, a radioopaque dye, or an enzyme.

7. The method according to claim 6, wherein said radionuclide is technetium 99.

8. The method according to claim 1, wherein said sample is a bodily fluid.

9. The method according to claim 8, wherein said bodily fluid is blood.

10. The method according to claim 9, wherein said monoclonal antibody is a humanized monoclonal antibody.

11. A kit for screening a sample to detect melanoma cells or prostate cancer cells, said kit comprising:
   (a) antibodies which bind specifically to a peptide having the amino acid sequence depicted in SEQ ID NO:1 or fragments of said antibodies, wherein said fragments bind specifically to said peptide; and
   (b) means for detecting the reaction of said antibodies with said melanoma cells or said prostate cancer cells.

12. A method for detecting the presence of melanoma or prostatic cancer in a human host, said method comprising:
   combining a sample from said human host with antibodies which are produced by a hybridoma cell line 12f3.2, having ATCC accession number HB11252, and detecting formation of immune complexes as indicataive of the presence melanoma cells or prostatic cancer cells.

* * * * *

UNITED STATES PATENT AND TRADEMARK OFFICE
CERTIFICATE OF CORRECTION

Figure 2:
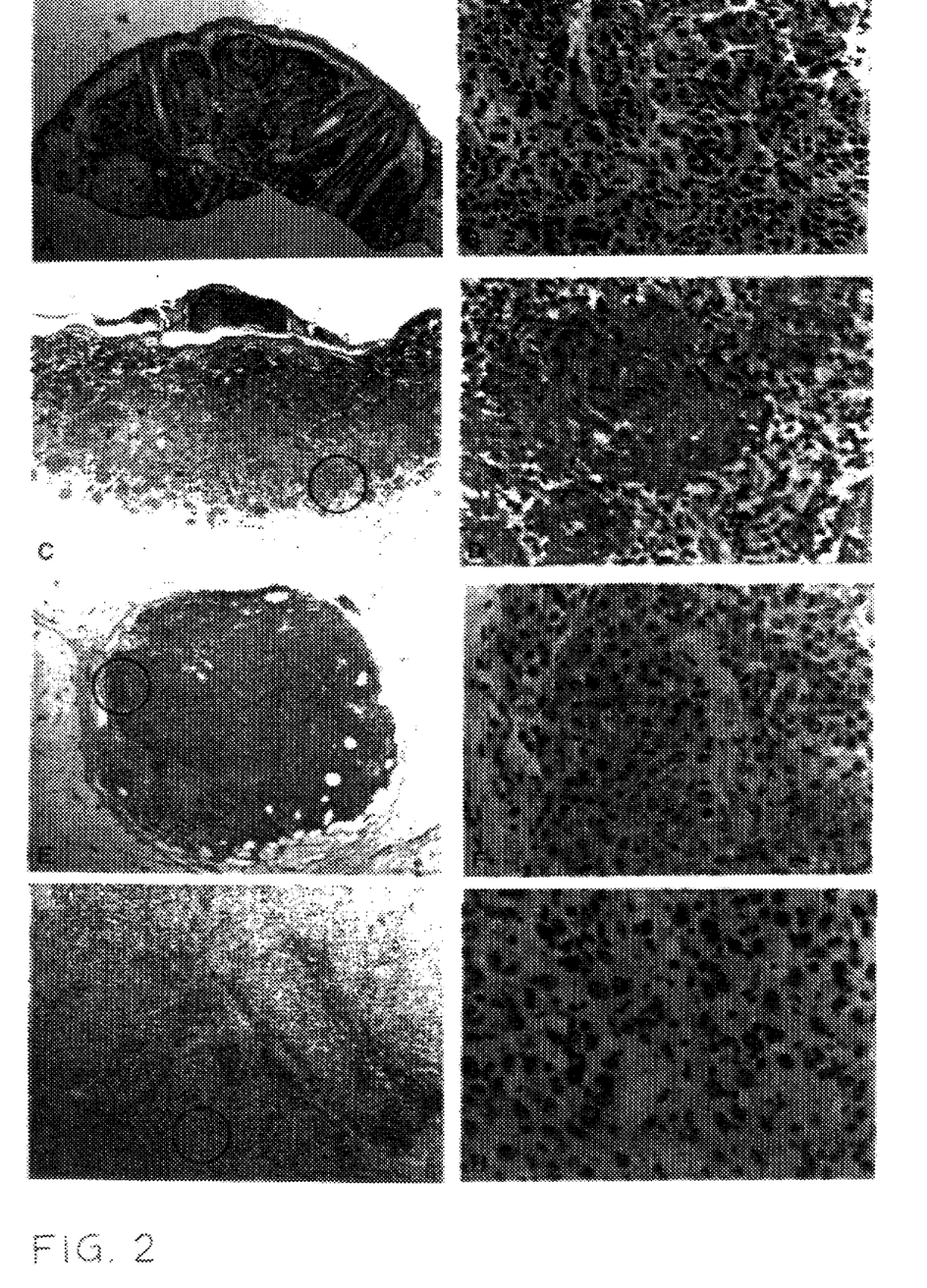
FIG. 2. Immunostaining of cross-sections from A,B) a common acquired nevus, C,D) a primary (vertical growth phase) melanoma, E,F) and G,H) melanomas metastatic to the skin with the monoclonal antibody XMEL. A) overview, 25×, B) 250× of inset in A) showing very weak, diffuse red positive staining of nevocytic cells with occasional punctate staining; C) overview, 25×, strong red staining in upper and lower areas of primary melanoma, weaker staining in the more central area, D) 250× of inset in C) showing the very strong, granular staining of nests of primary melanoma cells; E) overview, 25×, staining appears to be stronger on the periphery than in the central part of the metastatic tumor, F) 250× of inset in E) showing diffuse staining of variable intensity on melanoma cells; G) overview, 25×, showing areas of the metastatic melanoma with variable but weak staining, H) 250× of inset in G) showing the weak diffuse and variable staining of the melanoma cells, occasionally a punctate staining can be seen. In all the sections from the various specimens no staining was observed on other cells including normal melanocytes. Immunostaining was performed with ABC peroxidase staining kit (Vector Lab.) and AEC (3-amino-9-ethylcarbazole, Sigma) as chromogenic substance; sections were counterstained with Mayer's hematoxylin.
Figure 3:
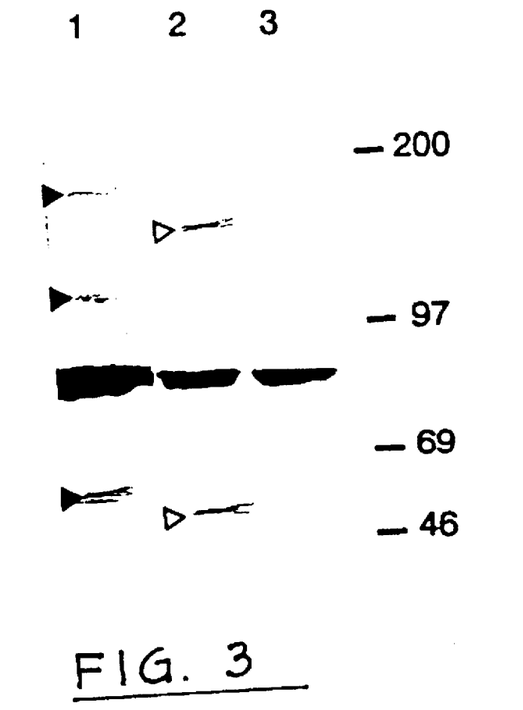
FIG. 3. Western blot analysis of proteins from cells of lane 1,3) Xiphophorus PSM and lane 2) human KZ13 melanoma cell line. Proteins in lane 1,2) were immunostained with XMEL hybridoma supernatant, rabbit anti-rat IgG(H+L) secondary antibody (Sigma) and DAB (3,3'-diaminobenzidine, Sigma) as chromogenic substance; proteins in lane 3) were reacted with hybridoma growth medium instead of XMEL supernatant. The XMEL monoclonal antibody stained faintly protein bands of 170,000, 115,000 and 60,000$M_r$ (closed triangles) in lysates from the PSM cells (lane 1) and stained faintly protein bands of 150,000 and 50,000$M_r$ (open triangles) in lysates from the KZ13 human melanoma cell line (lane 2). The strong protein band which appears in all 3 lanes most likely represents cross-reactivity with the growth medium and/or secondary antibody as it also appears in proteins from the PSM cells when the XMEL supernatant is replaced with the growth medium in the immunostaining reaction (lane 3). Numbers on the right side represent $M_r \times 10^3$ of rainbow protein marker (Bio Rad).

PATENT NO. : 5,719,032
DATED : February 17, 1998
INVENTOR(S) : Juergen R. Vielkind It is certified that error appears in the above-identified patent and that said Letters Patent is hereby corrected as shown below:

Column 10, line 33: after "cells" insert --(upper area in Fig. 2c)--

Signed and Sealed this

Third Day of October, 2000

Attest:

Q. TODD DICKINSON

*Attesting Officer*                    *Director of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 1:

```
Leu  Phe  Arg  Ser  Glu  Asp  Gln  Ser  Ile  Glu
 1              5                        10
```

( 2 ) INFORMATION FOR SEQ ID NO:2:

( i ) SEQUENCE CHARACTERISTICS:
        ( A ) LENGTH: 124 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 2..124

( x i ) SEQUENCE DESCRIPTION: SEQ ID NO:2:

```
C ACG CTG CAG CTG CGC TAC GCC AAC ACC ATC AAC TGG AGG CGC TTG        46
  Thr Leu Gln Leu Arg Tyr Ala Asn Thr Ile Asn Trp Arg Arg Leu
   1               5                  10                  15

TTC CGG TCT GAG GAC CAG AGC ATA GAG TAT GAC GCC AGG ACT GAG AAT      94
Phe Arg Ser Glu Asp Gln Ser Ile Glu Tyr Asp Ala Arg Thr Glu Asn
             20                  25                  30

CAA ACC TGC AAC AAC GAG TGC TCA GAG GAT                              124
Gln Thr Cys Asn Asn Glu Cys Ser Glu Asp
```

( 2 ) INFORMATION FOR SEQ ID NO:3:

( i ) SEQUENCE CHARACTERISTICS:
      ( A ) LENGTH: 41 amino acids
      ( B ) TYPE: amino acid
      ( D ) TOPOLOGY: linear ( i i ) MOLECULE TYPE: protein ( x i ) SEQUENCE DESCRIPTION: SEQ ID NO:3:

```
Thr Leu Gln Leu Arg Tyr Ala Asn Thr Ile Asn Trp Arg Arg Leu Phe
 1               5                  10                  15
Arg Ser Glu Asp Gln Ser Ile Glu Tyr Asp Ala Arg Thr Glu Asn Gln
                20                  25                  30
Thr Cys Asn Asn Glu Cys Ser Glu Asp
                35                  40
```